United States Patent [19]

Muz

[11] Patent Number: 5,048,533
[45] Date of Patent: Sep. 17, 1991

[54] METHOD AND APPARATUS FOR A NON-INVASIVE EXAMINATION OF BLOOD CIRCULATION IN A LIVING ORGANISM

[75] Inventor: Edwin Muz, Reutlingen, Fed. Rep. of Germany

[73] Assignee: Nicolay GmbH, Fed. Rep. of Germany

[21] Appl. No.: 400,719

[22] Filed: Aug. 30, 1989

[30] Foreign Application Priority Data

Aug. 31, 1988 [DE] Fed. Rep. of Germany ....... 3829456

[51] Int. Cl.⁵ ............................................. A61B 5/021
[52] U.S. Cl. .................................................. 128/679
[58] Field of Search ...................... 128/679, 680–683, 128/687

[56] References Cited

U.S. PATENT DOCUMENTS

| | | | |
|---|---|---|---|
| 3,104,661 | 9/1963 | Halpern | 128/679 |
| 4,172,450 | 10/1979 | Rogers et al. | 128/679 |
| 4,699,152 | 10/1987 | Link | 128/677 |
| 4,800,892 | 1/1989 | Perry et al. | 128/679 |
| 4,846,189 | 7/1989 | Sun | 128/679 |
| 4,873,987 | 10/1989 | Djordjevich et al. | 128/672 |

FOREIGN PATENT DOCUMENTS

| | | |
|---|---|---|
| 0060252 | 9/1982 | European Pat. Off. |
| 0073123 | 3/1983 | European Pat. Off. |
| 0024772 | 6/1984 | European Pat. Off. |
| 2152688 | 4/1973 | Fed. Rep. of Germany |
| 2751004 | 5/1978 | Fed. Rep. of Germany |
| 3100610 | 7/1982 | Fed. Rep. of Germany |
| 3345739 | 7/1985 | Fed. Rep. of Germany |
| 3723880 | 1/1989 | Fed. Rep. of Germany |

Primary Examiner—Lee S. Cohen
Assistant Examiner—K. M. Pfaffle
Attorney, Agent, or Firm—Wigman & Cohen

[57] ABSTRACT

A method and apparatus for the non-invasive examination of the blood circulation of a living organism uses a device having: a pair of sensors (18, 19), each of which detects the value $\beta$ (t) of a measurement value that changes during one pulse wave with the blood pressure of the organism and thereby with time, and transmits this value through signals; a pair of pressure sleeves for connecting the sensors with tissue of the organism through which arterial blood flows; and an electrical unit (21) for evaluating the signals of the mentioned sensors. The method includes setting two subdiastolic pressures which differ from each other by a small value in the two sleeves, transmitting signals obtained from the two sensors (18, 19) to the evaluating unit (21), and determining a circulatory function of the organism from transmitted signals in the evaluating unit.

13 Claims, 2 Drawing Sheets

METHOD AND APPARATUS FOR A NON-INVASIVE EXAMINATION OF BLOOD CIRCULATION IN A LIVING ORGANISM

BACKGROUND OF THE INVENTION

1. Field of the Invention

The invention relates to a method for a non-invasive examination of blood circulation in a living organism.

The measurement values of the blood circulation of a living organism such as a human being can be obtained on a continuous basis by means of invasive methods. In these methods a blood vessel is opened and a monitoring probe is introduced. In order to avoid the risk of infection, the use of non-invasive methods is desired for long-term monitoring.

Accordingly, it is known from Riva-Rocci and Korotkoff to automate the auscultation. In this monitoring method a sleeve, also called cuff, is placed at a given location on the examination subject (generally on the upper arm), where the pulsating flow of the arterial blood can be detected, e.g., by sound. The sleeve pressure is first set to a value that cuts off the flow of blood. The measurement of the diastolic and systolic pressure is made as the sleeve pressure falls. The cutting off of the flow of blood places a severe stress on the subject. The measurement can therefore only be performed as a single measurement and cannot be performed as a continuous monitoring of the circulatory system.

DE-OS 27 33 776 discloses a method for monitoring the pulse curve in which a sleeve is placed on the subject with a sensor for the sleeve pressure, which converts the measurement value into electrical values which are then evaluated oscillometrically. In this known method the sleeve pressure is put in place with a pressure that is less than the diastolic pressure of the subject, thus enabling a continuous monitoring of the pulse curve. The values of the diastolic, average, and systolic pressures can then be determined from the pulse curve. The following equation is valid for the sleeve pressure:

$$P_M = P_{Bl} - P_{TM} \quad (1)$$

wherein:
$P_M$ = sleeve pressure
$P_{Bl}$ = blood pressure
$P_{Tm}$ = transmural pressure.

Transmural pressure denotes the difference in pressure inside and outside a blood vessel. The expansion of the blood vessels due to transmural pressure is dependent not only on the age of the specific subject, but also on the temperature, muscle tone and nervous condition. These interrelationships are not fully understood. The pulse curve therefore does not offer a possibility for determining the actual curve of the blood pressure.

EP-PS 60 252 discloses a method in which the unknown function of the interrelationships of blood vessel expansion is eliminated from the blood pressure. In this method, light absorption is measured in the tissue of a finger of the subject and the sleeve pressure is automatically regulated in such a manner that the sleeve volume and thus also the blood vessel volume remain constant. This has the result, however, that despite the increase in blood pressure, the blood flow in the arteries located beneath the pressure of the sleeve is held constant, which places stress on the circulation of the subject and therefore cannot be used for long-term monitoring. Aside from this, the pressure in the sleeve must be regulated immediately, which necessitates a very expensive and complicated apparatus.

EP patents 152 848 and 188 894 disclose the use of a measurement with one or two sleeves at different pressures in a calibration phase, prior to a continuous monitoring of the blood circulation with one sleeve pressure below the diastolic blood pressure. Based on these measurements, parameters are thus established for determining the characteristics of the blood vessel walls.

Both methods share the disadvantage that the connection between blood pressure and blood vessel volume, as mentioned above, also depends, among other things, on the temperature, muscle tone and the nervous condition of the subject, and these factors can change very rapidly, especially with an ill subject. For example, a person in shock experiences a so-called vasorestriction, a constriction of the peripheral blood vessels, which has the effect that the brain is assured of an adequate supply of oxygen. All of these changes make it impossible with the known methods to perform a reliable, continuous monitoring of the circulatory system of a subject. In order to achieve an approximately precise representation of the actual circumstances, the calibration phase would have to be repeated often within short time frames, which would amount to a significant stress on the subject.

The above statements are valid even if the measurements are performed oscillometrically in accordance with the method in DE-OS 27 33 776, or in accordance with the methods contained in EP patents 24 772, 60 252 or 73 123 through the determination of light absorption.

DE-PS 21 52 688 discloses a method for the noninvasive measurement of the diastolic blood pressure, in which two sleeves are employed, the pressure chambers of which are connected with a common pressure discharge, operate with the same sleeve pressure, and are connected with each other by an intermediate indicator for pressure changes of flows. I this known method, these sleeves are placed at two points on the subject, one behind the other, on the same flow of arterial blood. The pulsing of the blood flow causes a pulsing expansion in the volume of the blood vessels surrounded by the sleeve, which results in a pulsing change in the sleeve pressure. When the instantaneous blood pressure falls below the sleeve pressure prevailing in the pressure chambers, there is a momentary closure of the blood vessels, or at least a significant reduction in the cross-sectional area thereof. This may result in different effects on the pulse-synchronous fluctuations in the blood vessel volume beneath the two sleeves, because behind the distal sleeve on the distal side lies a substantial volume of blood vessels and cell tissue which are blocked from the heart during the closure. The resulting differences in the instantaneous values of the pulsing change in sleeve pressure are displayed by the indicator. During the measurement, as the sleeve pressure falls, if the sleeve pressure becomes equal to or less than the diastolic pressure, then time-synchronous and equal quantity changes in blood vessel volume occur under both sleeves, and the indicator shows a minimum of its measurement value for the precise designation of the moment at which the sleeve pressure has reached the diastolic pressure.

In this known method it therefore depends on establishing the point at which the countervailing influences of two sleeves placed on a flow of blood cease.

DE-AS 27 51 004 discloses a device for vein closure plethysmography, in which a plurality of pressure sleeves are placed on one flow of blood. Here, too, one depends on the opposing influences of these sleeves so that the instantaneously measured sleeve pressures, which indicate blood pressure, are different in the two successively placed sleeves, as in the prior art described above in DE-PS 21 52 688.

Both in the known methods and in the method according to the invention, pressure sleeves are employed, having walls that are flexible but do not stretch under the pressures exerted during measurement.

SUMMARY AND OBJECT OF THE INVENTION

The object of the invention is to provide a method for the noninvasive examination of the blood circulatory system of a living organism by means of which the circulatory system can be monitored continuously over long periods of time without interruption.

This object is achieved with a device having at least one sensor (18, 19), which detects the value $\beta(t)$ of a measurement value that varies during one pulse wave with the blood pressure $P_{BL}$ of the organism and thereby with time, and transmits this value through signals, at least one pressure sleeve for connecting the mentioned sensor with tissue of the organism through which arterial blood flows, and an electrical unit (21) for evaluating the signals of the mentioned sensor, by the following method steps:

a) that a blood pressure value of the mentioned organism is determined that is independent of transmural pressure, b) that one such sensor is placed at each of two locations on the cited organism by means of such a cited sleeve, said locations having arterial blood flowing through them and being connected as in parallel, in order to be able simultaneously to perform the mentioned investigation with the two mentioned sensors of the two mentioned sleeves, the pressures of which are capable of being regulated independently of each other, c) that with equal pressures in the two mentioned sleeves, the mentioned device is adjusted so as to display equal values $\beta_1(t)$ and $\beta_2(t)$ of the mentioned measurement values on the display, d) that pressures $P_{M1}$ and $P_{M2}$ are set in the two mentioned sleeves, which differ from each other by a small value Delta $P_M$ and whose values are smaller than the diastolic blood pressure, and e) that a sought circulatory function is determined from the mentioned signals of the mentioned time-variable values $\beta_1(t)$ and $\beta_2(t)$ of the mentioned measurement values that are transmitted to the mentioned evaluating unit (21) from the two mentioned sensors (18, 19).

By means of the method step a), first the device is set to a directly measured blood pressure value of the organism as a reference value. One blood pressure value that is independent of the transmural pressure is the systolic pressure, at which the transmural pressure=0. The systolic pressure indicates when the actual blood pressure is equal to the sleeve pressure, namely when the arteries closed off by the suprasystolic pressure begin to open and the Korotkoffic sounds can be heard. A different blood pressure value that is independent of the transmural pressure, where the transmural pressure is also=0, is the diastolic pressure, namely the lowest pressure during one pulse wave, when the arteries assume their normal, non-tensed condition. Because these blood pressure values correspond to the measured sleeve pressure, they need only be measured once with a subject in order to perform the method according to the invention.

The method step b) is required in order to eliminate the unknown dependence of the blood pressure on blood vessel volume, as the mathematical progression below demonstrates.

Through the use of sleeve pressures, which, according to method step d), are smaller than the diastolic blood pressure, the circulatory monitoring can be performed noninvasively over a long period of time without placing stress on the subject.

Through method step c) the device is only adjusted so that the two sensors contained in the two sleeves under equal sleeve pressure in the device lead to the same displays. Accordingly, this is simply an adjustment of the device which will not vary as a result of changes in transmural pressure and blood vessel expansion, thus making a calibration phase unnecessary.

Through method step e), the desired circulatory function is calculated from the signals transmitted by the sensors from the changes over time of the measurement values $\beta_1(t)$ and $\beta_2(t)$, and are displayed in any manner desired. The signal processing can take place by means of analog or digital technology. Suitable circuits in analog technology and algorithms in digital technology are known and are not the object of the invention. Correspondingly, an electrical circuit or a computer can be used as an electrical evaluating unit.

In one advantageous embodiment of the method according to the invention a circuit is used or a computer serving as an evaluating unit implements an algorithm, and through its assistance the differential quotient of the blood pressure is determined as a function of time according to the formula $$dp_{B1}(t)/dt = \text{Delta } p_M * d\beta_1(t)/dt : <\beta_2(t) - \beta_1(t)> \qquad (2)$$

and this is integrated to give the blood pressure curve $P_{B1}(t)$.

The above formula (2) results from the following mathematical derivation, in which the following symbols are used for the cited concepts:

$P_{B1}(t)$ = the blood pressure changing with time (t) during one pulse wave, $V_M(t)$ = the sleeve volume which changes with t with the opposite sign, $P_M(t)$ = the sleeve pressure, which changes $V_M(t)$ and therefore with $P_{B1}(t)$, $P_{Tm}(t)$ = the transmural pressure, the pressure in the blood vessel that tends to counteract the blood pressure $P_{B1}(t)$.

In order to avoid difficulties in calculation, all of these values are made dimensionless by division with a certain reference volume $V_O$ or a reference pressure $P_O$, so that above in the formula (2) and in the following mathematical derivation, the symbols described with capital letters are replaced by symbols described with lower case letters as follows:

$$p_i(t) = P_i(t) : P_O \text{ and } v_i(t) = V_i(t) : V_O \qquad (3),$$

wherein i signifies the indicia B1, Tm, and M.

In order to simplify the writing style below, the parenthetical expression (t) indicating the variability of the respective value over time will be omitted to the extent that such omission will not inhibit clarity.

The sleeve volume $V_M$ is significantly larger than the volume of the blood vessels surrounded by the sleeve, so that even large changes in blood vessel volume and thus in blood pressure PB1 cause only minimal changes in the sleeve volume and thus cause minimal changes in the sleeve pressure $P_M$. From (1) and (3) it therefore follows that $$dp_{Tm}/dt = dp_{B1}/dt \quad (4)$$

The quantity of blood filling the blood vessels and blood vessel volume vary with the blood pressure $P_{B1}$ which itself varies during a pulse wave, and with these there also varies a detectable measurement value $\beta(t)$ which is dependent on these values, such as the sleeve pressure $P_M$, radiation permeability, electrical conductivity, the magnetic characteristics caused by the iron content of the hemoglobin, etc.

It is noted that although the quantity of blood filling the blood vessels is proportional to the volume of the blood vessels it has a different physical effect namely, e.g., the quantity of blood on the translucence (or absorption) of a radiation and the volume on the pressure in the cuff.

With the awareness of the unknown functional relationship between such a measurement value $\beta$ and the transmural pressure $P_{Tm}$, the fluctuations of $\beta$ could permit fluctuations in blood pressure $P_{B1}$ to be determined. It is demonstrated below how the placement of two sleeves having sleeve pressure $$p_{M2} = p_{M1} - \text{Delta } p_M \quad (5)$$

that differ from each other by a small value Delta $P_M$ can eliminate this unknown functional relationship between $\beta$ and the transmural pressure $P_{Tm}$.

Therefore, for this function we first add the statement $$\beta = p_{Tm} * f(p_{Tm}) \quad (6)$$

where f ($p_{Tm}$) is any desired unknown function of transmural pressure $p_{Tm}$ and * multiplication sign.

By differentiating (6) over time, we obtain $$d\beta/dt = dp_{Tm}/dt * (f + p_{Tm} * df/dp_{Tm}) \quad (7)$$

From formula (4) it follows that $$d\beta/dt = dp_{B1}/dt * (f + p_{Tm} * df/dp_{Tm}) \quad (8)$$

Because the measurements with the two pressure sleeves with the two different pressures $P_{M1}$ and $P_{M2}$ are performed simultaneously at different but similar extremities, the same blood pressure is present during measurement according to method step d). Formula (1) in conjunction with the definition (3) thus yields the two following equations:

$$p_{M1} = p_{B1} - p_{Tm1}$$

and $$p_{M2} = p_{B1} - p_{Tm2}$$

If we then form the difference $p_{M1} - p_{M2} = \text{Delta } p_M$ then the following formula results:

$$p_{Tm2} = p_{Tm1} + \text{Delta } p_M \quad (9)$$

If we develop the function f($p_{Tm}$+Delta $p_M$) into a Taylor series, then with a sufficiently small Delta $p_M$ this series can be interrupted after the second member to obtain the formula $$f(p_{Tm1} + \text{Delta } p_M) = f(p_{Tm1}) + (\text{Delta } p_M) * {}^*df(p_{Tm1})/dp_{Tm1} \quad (10)$$

From formulas (6), (9) and (10), the following equations then result for the two measurement values $\beta 1$ and $\beta 2$, which in the two pressure sleeves are measured at the different sleeve pressures $P_{M1}$ and $P_{M2}$:

$$\beta_2(t) = (p_{Tm1} + \text{Delta } p_M) * \quad (11)$$

$$< f(p_{Tm1}) + \text{Delta } p_M * df(p_{Tm1})/dp_{Tm1} > = p_{Tm1} * f(p_{Tm1}) +$$

$$\text{Delta } p_M * p_{Tm1} * df(p_{Tm1})/dp_{Tm} + \text{Delta } p_M * f(p_{Tm1}) +$$

$$(\text{Delta } p_M)^2 * df(p_{Tm1})/dp_{Tm1}$$

$$\beta_1(t) = p_{Tm1} * f(p_{Tm1})$$

In equation (11), With a sufficiently small Delta $p_M$ the last member can be eliminated. For the difference of the two $\beta$-values, the following expression thus results:

$$\beta_2 - \beta_1 = \text{Delta } P_M(P_{Tm1}*df(p_{Tm1})/dp_{Tm1} + \text{Delta } p_M*f(p_{Tm1}) \quad (12)$$

From formula (8), the following expression then follows for the product of the second and third factors of the first member of equation (12):

$$p_{Tm1}*df/dp_{Tm1} = <d\beta_1/dt - dp_{B1}/dt*f(p_{Tm1})> :d-p_{B1}/dt \quad (13)$$

If the expression (13) is then inserted into equation (12), then one obtains the above-mentioned formula (2) for the differential quotient of the blood pressure over time.

Because the value for Delta $\beta_M$ is predetermined and both the value $d\beta_1/dt$ and the difference $\beta_2 - \beta_1$ can be determined at any given moment by measurement and calculation, this formula also permits the momentary differential quotient of blood pressure to be calculated which integrated results in the function $\beta_{B1}$ (t) of blood pressure, from which through multiplication with the reference value $P_O$ and through the use of the blood pressure value determined according to method step a), the time curve of the blood pressure $P_{B1}$ (t) can be calculated.

As the degree to which the blood vessels are filled with blood varies during a pulse wave, the radiation permeability of the tissue through which the arterial blood flows also varies. As a measurement value one can therefore, in a known manner, also use the photoelectric current that is produced when an opto-electric system consisting of a radiation sender and a radiation sensor is used to ascertain the radiation permeability in each sleeve. This variant of the method according to the invention also makes possible the following advantageous embodiment. In the book "Non-Invasive Measurements" of the publishing house Academic Press, Inc. 1983 in the chapter "NON-INVASIVE SPECTROPHOTOMETRIC ESTIMATION OF ARTERIAL OXYGEN SATURATION" by I. Yoshiya and Y.

Shimada, a method for determining the oxygen saturation of blood is described in which simultaneously one beam of a first wave length range and a second beam in a second wave length range, in which the absorption coefficients of oxi-hemoglobin and reduced hemoglobin stand in different ratios to each other, are radiated into living tissue and the mixed residual beam exiting the radiated tissue are received by means of two optoelectronic receivers in the two wave length ranges and measured, and on the basis of the measured intensities of the residual radiations of the two wave ranges, the oxygen saturation of the blood is determined The method according to the invention can thus be set u in such a manner that in addition to the above-described determination of the desired circulatory values, simultaneously the oxygen content of the blood is determined, in that an additional optoelectronic system is used in one sleeve, and is operated with radiation in a different wave length.

The invention also relates to a device for the non-invasive examination of the blood circulatory system of a living organism with two pressure sleeves, with an optoelectronic system for an equivalent wave length range in each sleeve, which system consists of a radiation sender and a radiation receiver, and having an electrical unit to evaluate the signals transmitted to it from the optoelectronic systems.

According to the invention, in this device an additional photoelectronic system for a wave length measurement range is provided in a sleeve, which range differs from the wave length measurement range of the other optoelectronic system such that with the two photoelectronic systems, one sleeve can also ascertain the oxygen content of the blood.

In order to subject the examinee to as little stress as possible, not only with regard to circulatory stress but also purely mechanical stress, as the method according to the invention is being performed, in a further advantageous device according to the invention it is provided that the pressure sleeves are formed as caps that can be placed on the ends of extremities, such as fingers, of the living organism. In this regard it is particularly advantageous to connect the two caps with each other to form a sleeve unit, and to provide for the caps to be placed on two adjacent extremities, e.g., on the ring finger and middle finger.

Two variations of the method according to the invention, and two exemplary embodiments of the devices according to the invention are described in detail below, with the assistance of the drawings:

DETAILED DESCRIPTION OF THE PREFERRED EMBODIMENTS

Figure 1:
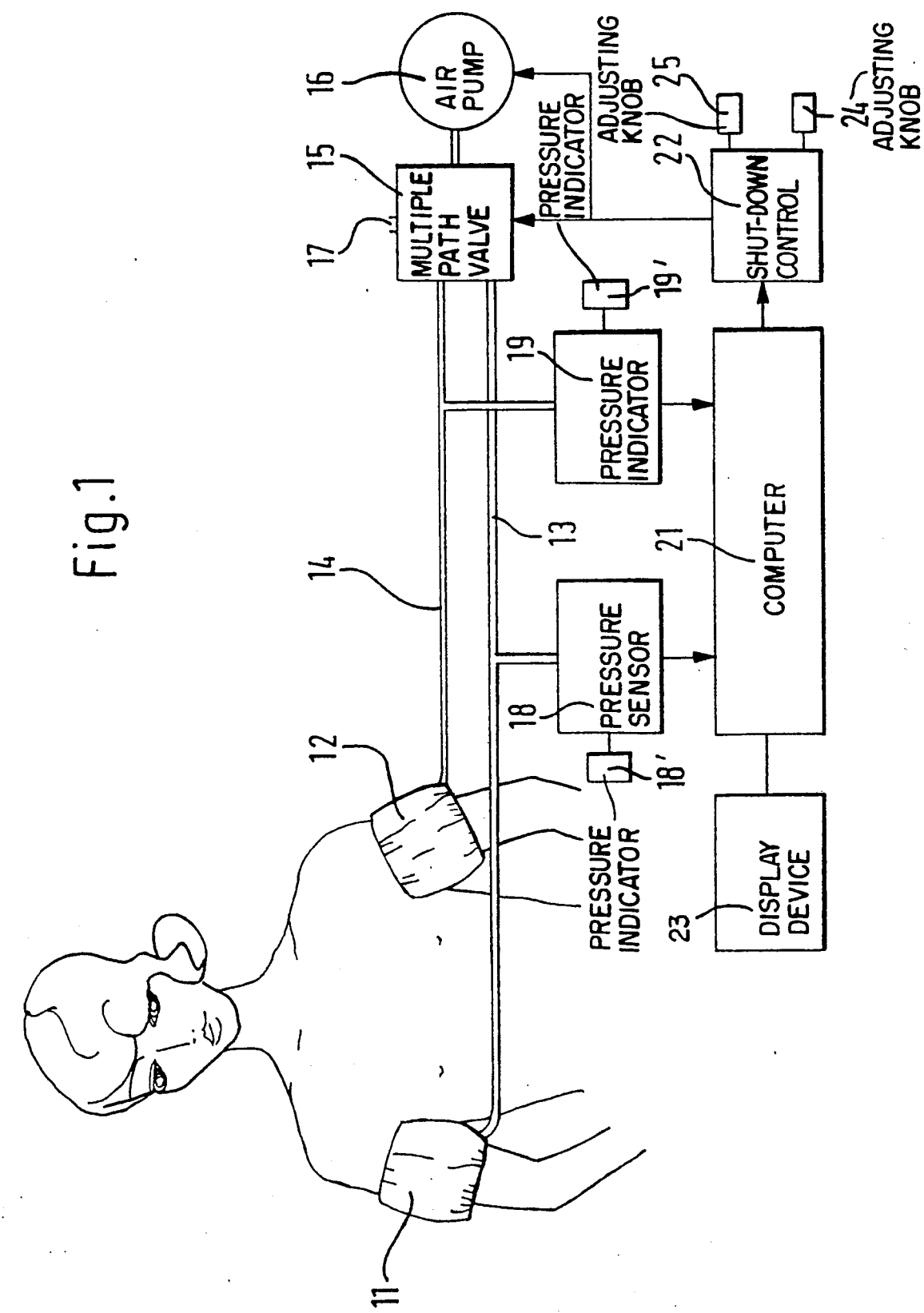
FIG. 1 is a schematic representation of a first exemplary embodiment of the device.

The device illustrated in FIG. 1 includes two sleeves 11 and 12 which, for example, can be placed on the two arms of the subject or examinee. Each of the two sleeves 11 and 12 is connected with an air pump 16 by means of a pressure line 13 or 14 via a multiple-path valve 15, by means of which each of the two sleeves 11 and 12 can be inflated separately via the valve 15. The multiple-path valve 15 is provided with a discharge opening 17 which can be selectively connected by the valve with one sleeve or the other in order to reduce an undesirable excess pressure and to establish a given desired pressure in each sleeve.

Each of the two pressure lines 13 and 14 is connected with respective pressure sensors 18 and 19, each of which can be associated with its own pressure indicator 18, and 19, These pressure sensors 18 and 19 are used to measure the sleeve pressure $P_M$ in the two sleeves 11 and 12. The sensors convert the pressure measurement into electric signals which are transmitted to a computer 21 serving as an electrical evaluating unit. A shut-down control 22 and a digital or oscillographic display device 23 are associated with the computer 21. The multiple-path valve 15 and the air pump 16 are controlled by means of the shut-down control. Respective adjusting knobs 24 and 25 are provided on the shut-down control 22 for each sleeve to enable the setting of certain pressures in the sleeves 11 and 12.

Figure 2:
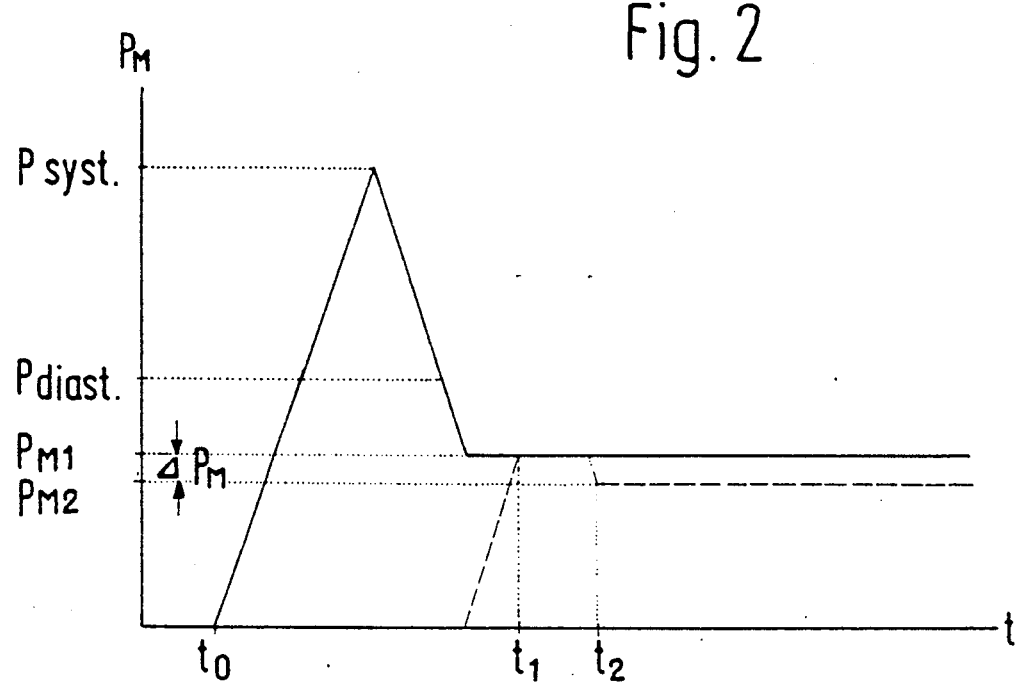
FIG. 2 is a diagram showing the time curve of the method, in which the pressure in one sleeve 11 is illustrated with a solid line and the pressure in the other sleeve 12 is illustrated with a broken line, and in which the pressure fluctuations caused by the pulse wave are left off for simplification of the drawings.

The course of the measurement process over time is explained in the diagram according to FIG. 2. At time point t the sleeve 11 is inflated until the pulse signal disappears at the systolic pressure. This pressure is stored by the computer 21 and displayed in the display device 23. Then the pressure in the sleeve 11 is reduced in order to determine the diastolic pressure in a known manner, which is also stored in the computer 21 and displayed in the display device 23.

Subsequently, both sleeves are inflated at time point t1 to an equal sleeve pressure $P_{M1}$ which lies below the diastolic pressure, for example at 40 mmHg. The signals emitted from the pressure sensors 18 and 19 are then equalized to the same values. At time point t2 the pressure in the sleeve 12 is reduced slightly by a small value Delta $P_M$ from about 2 to 14 mmHg to the value $P_{M2}$, and the device is then set for a monitoring of the blood circulation of the examinee for an indeterminate period.

In order to determine the course of blood pressure over time from the signals supplied by the sensors 18 and 19 to the computer 21, an algorithm according to the formula $$dp_{B1}/dt = \text{Delta } p_M \cdot dp_{M1}/dt : (p_{M2} - p_{M1})$$

is implemented in the computer 21, which formula is derived from the general formula (2) when the sleeve pressures P are used for the measurement values $\beta$. The implementation can take place in a known manner, either through appropriate design of the hardware or by programming.

In addition, known algorithms were implemented in the computer in order to integrate the differential quotients of the blood pressure resulting from the above-referenced algorithm and to display the obtained signals in analog by curves or by digital technology by numbers, whereby the absolute position of the blood pressure curve or the absolute value of the numbers are determined with the aid of the systolic or diastolic pressure value stored in the computer.

The monitoring of the blood circulation of the examinee performed in this manner can be performed uninterrupted for an indeterminate, long period of time, without placing stress on the examinee and his circulation.

Figure 3:
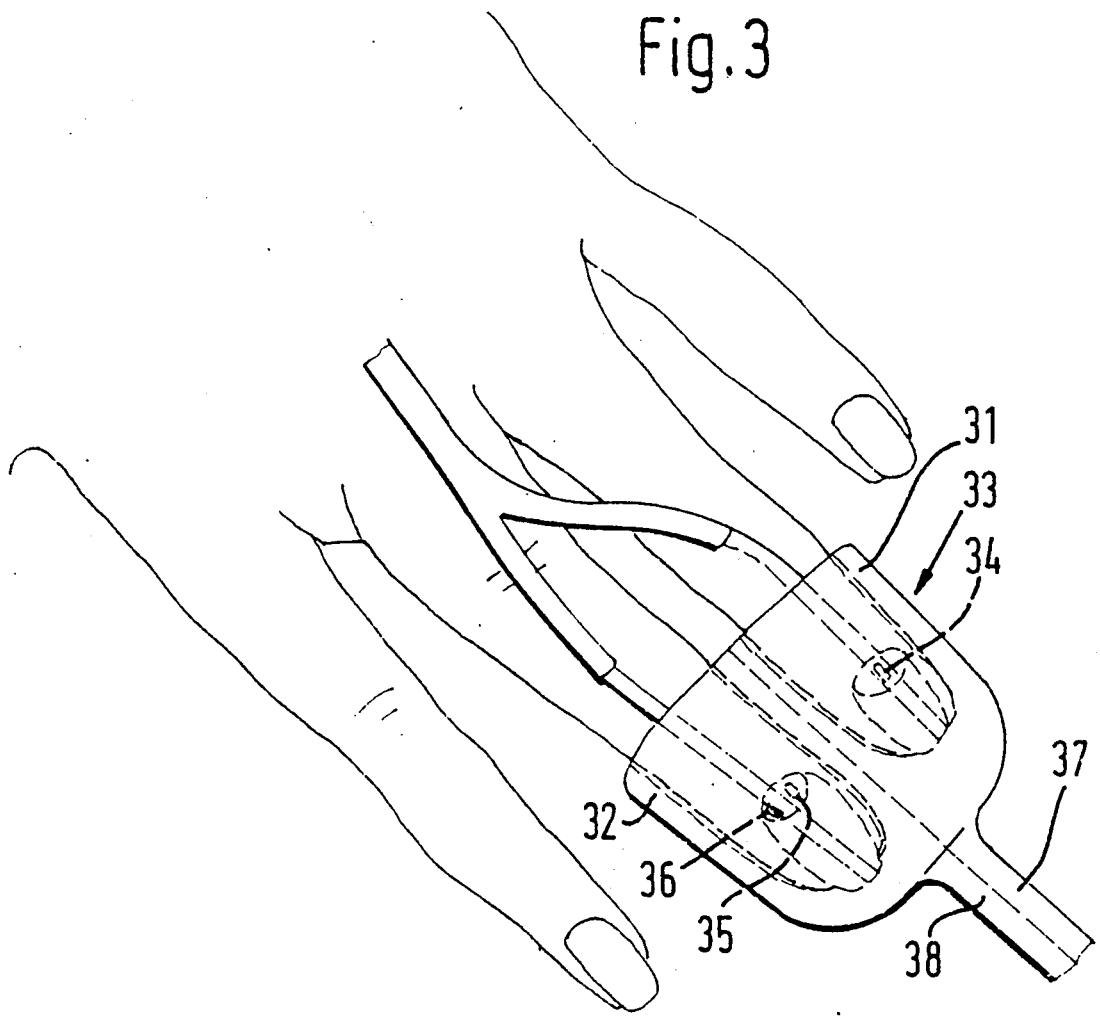
FIG. 3 is a view of a sleeve unit of the second exemplary embodiment.

In FIG. 3 there is shown a second variation of the method according to the invention, using a specially formed sleeve unit 33 consisting of two sleeves 31 and 32. The two sleeves 31 and 32 are formed as caps that can be placed over the end portion of the ring and middle fingers. Both sleeves are connected with each other to form the sleeve unit 33 Each of the two sleeves has an optoelectronic system 34 or 35, which consists in a known manner of a radiation sender (not shown in the drawing) and a radiation sensor, whereby the radiation sender beams radiation, e.g., light, into the tissue through which arterial blood flows, and the residual radiation passing out of the tissue is then received by the radiation sensor. The radiation sensor can be formed as a photoresistor. The current i flowing through it then forms the measurement value. Accordingly, an algorithm must be implemented into a computer corresponding to the computer 21 in FIG. 1, in which the measurement value in the general formula (2) is replaced by the current i flowing through the photoresistor. Accordingly, for this variation of the method according to the invention, the following formula follows $$dp_{B1}/dt = \text{Delta } p_M \cdot di_1/dt:(i_2 - i_1)$$

where i and i are the electrical currents controlled by the residual radiation and flowing through the two radiation sensors in the two optoelectronic systems 33 and 34. The adjustment and detection processes occur in the same manner as that described in the exemplary embodiment illustrated on the basis of FIG. 1.

The exemplary embodiment illustrated in FIG. 3 differs from the exemplary embodiment illustrated in FIG. 1 essentially only by the fact that here an additional, second optoelectronic system 36 is provided in the pressure sleeve 32, in which a radiation of a different wave length is used as in the optoelectronic system 34 and 35. Red light in a wave range of 614 to 660 nm can be selected as the radiation for the two optoelectronic systems 34 and 35. Infrared radiation in a wavelength range of 800 to 950 nm can then be used for the optoelectronic system 36. The device then makes it possible with the optoelectronic systems 34 and 35 of both sleeves 31 and 32, to determine the blood pressure curve of the examinee. Simultaneously, however, the oxygen saturation of the blood can be measured with the sleeve 32 having the two optoelectronic systems 35 and 36. A particular advantage of this device is that the elements of the optoelectronic systems are tightly hold on to the outer surface of the skin so that artifacts are avoided.

As can also be seen in FIG. 3, each sleeve 31 and 32 is connected with a pressure line 37 and 38 which are controlled in the same manner as was described above in connection with FIG. 1. The elements of the optoelectronic systems 34, 35 and 36 are connected with an electrical evaluating unit corresponding to the computer 21, by means of electrical leads of a cable 39. Details of the design of the optoelectronic systems and the evaluation of their displays are part of the prior art.

For the measurements with sleeve pressures that lie below the diastolic blood pressure, with children the sleeves can be put in place with sleeve pressures of from 10 to 40 mmHg, and with adults with sleeve pressures of from 20 to 60 mmHg. The difference in pressure between the two sleeves can be adjusted thereby to values of from 2 to 15 mmHg.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for non-invasive determination of the actual blood pressure $P_M(t)$ of a living organism as a function of time, which blood pressure changes in a range comprising a diastolic and a systolic pressure, at locations of said organism which contain arteries which change their volumes dependent on said actual blood pressure and on a transmural pressure caused by said arteries;

by an apparatus which comprises:

first and second pad means, each for applying a pressure $P_{M1}$ and $P_{M2}$, respectively, to a first and a second of said locations of said organism and each having a chamber with a volume for a pressure means for producing said pressure $P_{M1}$ and $P_{M2}$, respectively, first and second control means for said first and second pad means for setting said pressures $P_{M1}$ and $P_{M2}$, respectively, independently from each other in each of said pad means, first and second sensor means for each of said first and second pad means, respectively, which sensor means respond to perceivable values $\beta_1(t)$ and $\beta_2(t)$, respectively, that change depending on said actual blood pressure and said transmural pressure and transmit signals which correspond to said values $\beta_1(t)$ and $\beta_2(t)$ and an evaluating means for evaluating said signals of said sensor means, said method comprising the steps of:

a) determining a blood pressure value of said organism which is dependent of said transmural pressure, b) applying said first and second pad means to said first and second locations of said organisms, the arteries of said first and said second locations being parallel to each other within said organism, in order to simultaneously perceive said values $\beta_1(t)$ and $\beta_2(t)$ in said first and second locations independently from each other, c) setting equal said pressures $P_{M1}$ and $P_{M2}$ applied by said first and said second pad means at each of said first and said second locations and adjusting said evaluating means for an output of equal said perceivable values $\beta_1(t)$ and $\beta_2(t)$ derived from said signals transmitted by said first and second sensor means, d) setting first and second predetermined pressures as said pressures $P_{M1}$ and $P_{M2}$ at each of said first and said second locations, said first and said second predetermined pressures being smaller than said diastolic pressure of said organism and differing from each other by a value Delta $P_M$ which is small compared with said diastolic pressure and actuating said first and said second sensor means for responding to said perceivable values $\beta_1(t)$ and $\beta_2(t)$, respectively, and for transmitting signals which correspond to said values, and evaluating said transmitted signals from said sensor means received by said evaluating means for determining the blood pressure of said organism as a function of time.

2. The method according to claim 1, comprising the steps of implementing in said evaluating means an algorithm by which the differential quotient of the blood pressure is determined as a function of time according to the formula:

$$dp_{B1}(t)/dt = \text{Delta } P_M + d\beta_1(t)/dt : <\beta_2(t) - \beta_1(t)> ; Ps$$

evaluating said differential quotient of said actual blood pressure from said signals; and integrating said differential quotient in order to determine the actual blood pressure $P_{B1}$ as a function of time.

3. The method according to claim 2, where said predetermined pressure $P_{M1}$ and $P_{M2}$ of said first and said second pad means, respectively, results in actual pad pressure which change dependent on said change of said volume of said arteries, comprising the steps of taking said actual pad pressures as said perceivable values $\beta_1(t)$ and $\beta_2(t)$.

4. The method according to claim 2, comprising the steps of taking the radiation permeabilities of said locations as said perceivable values $\beta_1(t)$ and $\beta_2(t)$.

5. The method according to claim 4, comprising:
a) determining said radiation permeabilities in each of said pad means using an optoelectronic system including a radiation transmitter and a radiation sensor; and
b) using the photoelectric current flowing in the radiation sensor as said perceivable values.

6. The method according to claim 5, further comprising:

simultaneously determining the oxygen content of the blood using an additional optoelectronic system in one of said pad means, said additional system being operated with radiation of a wavelength different from the wavelength at which said optoelectronic system determining the radiation permeabilities is operated.

7. The method according to claim 1, wherein said predetermined pressures $P_{M1}$ and $P_{M2}$ are set in the range from 10 to 40 mmHg when used on children, and are set in the range from 20 to 60 mmHg when used on adults, and said value Delta $P_M$ is set in both cases in the range from 2 to 15 mmHg.

8. Apparatus for non-invasive determination of the actual blood pressure of a living organism as a function of time, comprising:

first and second pad means for applying predetermined pressures $P_{M1}$ and $P_{M2}$ to first and second locations of said organism, respectively, which locations contain arteries which change their volume depending on said actual blood pressure and a transmural pressure caused by said arteries, first and second sensor means for each of said first and second pad means for transmitting first and second signals corresponding to perceivable values $\beta_1(t)$ and $\beta_2(t)$, respectively, which values change dependent on said actual blood pressure and said transmural pressure, means for evaluating said signals comprising computer means for implementing an algorithm connecting means connecting said first and said second sensor means to said evaluating means for transmitting said signals to said evaluating means, wherein in said computer means said algorithm is implemented by which the differential quotient of the blood pressure is determined as a function of time according to the formula:

$$dp_{B1}(t)/dt = \text{Delta } P_M \cdot d\beta_1(t)/dt : <\beta_2(t) - \beta_1(t)>$$

so that said differential quotient is computed as a function of time from said signals received from said sensor means in said computer means which is adapted to integrate said differential quotient to determine the actual blood pressure $P_M(t)$ as a function of time.

9. The apparatus according to claim 8, wherein said first and said second sensor means each comprises an optoelectronic system with a transmitter and a receiver for a radiation which is partly absorbed in said first and said second locations of said organism dependent on said volume of said arteries, so that said partial absorptions in said first and said second locations form said perceivable values $\beta_1(t)$ and $\beta_2(t)$, respectively.

10. The apparatus according to claim 9, in which one of said first or second pad means includes;

an additional sensor means comprising an additional optoelectronic system with an additional transmitter and receiver for an additional radiation which is different from said radiation of said first and second sensor means, so that said additional sensor means emits an additional signal caused by a partial absorption of said additional radiation; and an electrical unit to determine a feature of the blood from both said additional signal and said first or said second signal of said sensor means which is included in the same of said first or second pad means, respectively.

11. The apparatus according to claim 10, wherein said first and said second pad means are formed as caps for placing them on the ends of two similar but distinct adjacent extremities of said living organism, said two pad means being connected to each other to form a pad means unit.

12. The apparatus according to claim 9, wherein said first and said second pad means are formed as caps for placing them on the ends of two similar but distinct adjacent extremities of said living organism, said two pad means being connected to each other to form a pad means unit.

13. The apparatus according to claim 8, wherein said first and said second pad means are formed as caps for placing them on the ends of two similar but distinct adjacent extremities of said living organism, said two pad means being connected to each other to form a pad means unit.

* * * * *

UNITED STATES PATENT AND TRADEMARK OFFICE
CERTIFICATE OF CORRECTION

PATENT NO. : 5,048,533

DATED : September 17, 1991

INVENTOR(S) : Edwin MUZ

It is certified that error appears in the above-identified patent and that said Letters Patent is hereby corrected as shown below:

IN THE SPECIFICATION:

Column 2, line 40 delete "I" and insert --In--.

Column 5, line 6, delete "PB1" and insert --$P_{B1}$--.

Column 6, line 26, delete "With" and insert --with--;

line 43, delete "$ß_M$" and insert --$P_M$--;

line 48, delete "$ß_{B1}$" and insert --$P_{B1}$--.

Column 7, line 14, delete "u" and insert --up--.

Column 8, line 13, delete "18, and 19," and insert --18' and 19'.--;

line 28, delete "t" and insert --$t_0$--.

UNITED STATES PATENT AND TRADEMARK OFFICE
CERTIFICATE OF CORRECTION

PATENT NO. : 5,048,533

DATED : September 17, 1991

INVENTOR(S) : Edwin MUZ

It is certified that error appears in the above-identified patent and that said Letters Patent is hereby corrected as shown below:

IN THE CLAIMS:

Claim 1, column 11, line 1 before "evaluating" insert --e)--.

Claim 2, column 11, line 10 delete "Ps" at end of line.

Claim 3, column 11, line 19, "pressure" should be --pressures--.

Signed and Sealed this

Second Day of February, 1993

Attest:

STEPHEN G. KUNIN

Attesting Officer

Acting Commissioner of Patents and Trademarks

UNITED STATES PATENT AND TRADEMARK OFFICE
CERTIFICATE OF CORRECTION

PATENT NO. : 5,048,533

DATED : September 17, 1991

INVENTOR(S) : Edwin Muz

It is certified that error appears in the above-identified patent and that said Letters Patent is hereby corrected as shown below:

IN THE DRAWINGS:

Fig. 1, numeral 19, delete "PRESSURE INDICATOR" and insert --PRESSURE SENSOR--.

Column 4, line 51, after "changes" insert --with--.

Column 5, line 45, immediately before the term "multiplication sign" insert --is the--.

Column 6, lines 8 and 9, first line of equation (10), delete first appearance of "*";

line 20, third line of equation (11), delete the factor "$df(P_{Tm1})/dp_{Tm}$" and replace with --$df(P_{Tm1})/dp_{Tm1}$--;

line 25, delete "With" and insert --with--; and line 29, delete first occurrence of "(" and insert --*--.

Column 9, line 9, after "unit 33" insert --.--;

line 28, delete "i and i" and insert --$i_2$ and $i_1$--;

lines 30 and 31, delete "33 and 34" and insert --34 and 35--.

Signed and Sealed this

Sixth Day of July, 1993

Attest:

MICHAEL K. KIRK

*Attesting Officer*  *Acting Commissioner of Patents and Trademarks*

UNITED STATES PATENT AND TRADEMARK OFFICE
CERTIFICATE OF CORRECTION

PATENT NO. : 5,048,533
DATED : September 17, 1991
INVENTOR(S) : Edwin MUZ It is certified that error appears in the above-identified patent and that said Letters Patent is hereby corrected as shown below:

IN THE DRAWINGS:

Fig. 1, numeral 19, delete "PRESSURE INDICATOR" and insert --PRESSURE SENSOR--.

Column 2, line 40 delete "I" and insert --In--.

Column 4, line 51, after "changes" insert --with--.

Column 5, line 6, delete "PB1" and insert --$P_{B1}$--;
       line 45, immediately before the term "multiplication sign" insert --is the--.

UNITED STATES PATENT AND TRADEMARK OFFICE
CERTIFICATE OF CORRECTION

PATENT NO. : 5,048,533

DATED : September 17, 1991

INVENTOR(S) : Edwin MUZ

It is certified that error appears in the above-identified patent and that said Letters Patent is hereby corrected as shown below:

Column 6, lines 8 and 9, first line of equation (10), delete first appearance of "*";

line 20, third line of equation (11), delete the factor "$df(P_{Tm1})/dp_{Tm}$" and replace with --$df(P_{Tm1})/dp_{Tm1}$--.

line 25 delete "With" and insert --with--;

line 29, delete first occurrence of "(" and insert --*--;

line 43, delete "$ß_M$" and insert --$P_M$--;

line 48, delete "$ß_{B1}$" and insert --$P_{B1}$--.

UNITED STATES PATENT AND TRADEMARK OFFICE
CERTIFICATE OF CORRECTION

PATENT NO. : 5,048,533
DATED : September 17, 1991
INVENTOR(S) : Edwin MUZ

It is certified that error appears in the above-identified patent and that said Letters Patent is hereby corrected as shown below:

Column 7, line 14, delete "u" and insert --up--.

Column 8, line 13, delete first occurrence of "18, and 19," and insert --18' and 19'.--;

line 28, delete "t" and insert --$t_0$--.

Column 9, line 9, after "unit 33" insert --.--;

line 28, delete "i and i" and insert --$i_2$ and $i_1$--.

lines 30 and 31, delete "33 and 34" and insert --34 and 35--;

UNITED STATES PATENT AND TRADEMARK OFFICE
CERTIFICATE OF CORRECTION

PATENT NO. : 5,048,533
DATED : September 17, 1991
INVENTOR(S) : Edwin MUZ It is certified that error appears in the above-identified patent and that said Letters Patent is hereby corrected as shown below:

Claim 1, column 11, line 1 before "evaluating" insert --e)--.

Claim 2, column 11, line 10, delete "Ps" at end of line.

Claim 3, column 11, lines 17 and 19, "pressure" should be --pressures--.

This certificate supersedes Certificate of Corrections issued June 2, 1993 and February 2, 1993.

Signed and Sealed this

Fourth Day of January, 1994

Attest:

BRUCE LEHMAN

*Attesting Officer*     Commissioner of Patents and Trademarks